United States Patent [19]
Porter

[11] Patent Number: 6,102,848
[45] Date of Patent: Aug. 15, 2000

[54] FLOW-AROUND VALVE WITH CONTOURED FIXATION BALLOON AND CHANNEL BLOCKING MEANS

[75] Inventor: Christopher H. Porter, Woodinville, Wash.

[73] Assignee: SRS Medical Systems, Inc., Burlington, Mass.

[21] Appl. No.: 09/189,951

[22] Filed: Nov. 12, 1998

Related U.S. Application Data

[63] Continuation-in-part of application No. 08/896,072, Jul. 17, 1997.

[51] Int. Cl.$^7$ .............................................. A61F 2/00
[52] U.S. Cl. ..................................................... 600/29
[58] Field of Search ........................................ 600/29, 31

[56] References Cited

U.S. PATENT DOCUMENTS

| | | |
|---|---|---|
| 2,494,393 | 1/1950 | Lamson . |
| 3,583,391 | 6/1971 | Cox et al. . |
| 3,630,206 | 12/1971 | Gingold . |
| 3,750,194 | 8/1973 | Summers . |
| 3,769,981 | 11/1973 | McWhorter . |
| 3,797,478 | 3/1974 | Walsh et al. ........................ 126/1 R |
| 3,841,304 | 10/1974 | Jones . |
| 3,908,635 | 9/1975 | Viek . |
| 4,386,601 | 6/1983 | Trick . |
| 4,419,985 | 12/1983 | Trick . |
| 4,579,554 | 4/1986 | Glassman . |
| 4,822,333 | 4/1989 | Lavarenne . |
| 4,878,901 | 11/1989 | Sachse . |
| 4,932,938 | 6/1990 | Goldberg et al. . |
| 4,994,066 | 2/1991 | Voss . |
| 5,030,199 | 7/1991 | Barwick et al. . |
| 5,088,980 | 2/1992 | Leighton . |
| 5,090,424 | 2/1992 | Simon et al. . |
| 5,096,454 | 3/1992 | Samples . |
| 5,112,306 | 5/1992 | Burton et al. . |
| 5,114,398 | 5/1992 | Trick et al. . |
| 5,306,241 | 4/1994 | Samples . |
| 5,483,976 | 1/1996 | McLaughlin et al. . |
| 5,513,659 | 5/1996 | Buuck et al. . |
| 5,591,145 | 1/1997 | Sachse . |
| 5,701,916 | 12/1997 | Kulisz et al. . |
| 5,713,861 | 2/1998 | Vanarthos . |

FOREIGN PATENT DOCUMENTS

| | | |
|---|---|---|
| 0 265 207 | 10/1987 | European Pat. Off. . |
| 2 595 564 | 3/1986 | France . |
| WO 97/06758 | 2/1997 | WIPO . |

*Primary Examiner*—Max Hindenburg
*Assistant Examiner*—Brian Szmal
*Attorney, Agent, or Firm*—Cesari and McKenna, LLP

[57] ABSTRACT

An incontinence system includes an anchoring mechanism and a channel with a blocking valve positioned in the channel, the blocking valve in a first state prevents urine flow through the channel and in a second state allows urine to flow through the channel. The anchoring mechanism may be a fixation balloon that is contoured to the geometry of the bladder near the opening to the urethra. When urine flows through the channel it flows around a lumen that provides access to the fixation balloon. The fixation balloon may be attached to a shortened Foley-type catheter, with the catheter providing the channel through the balloon. The catheter may contain a lumen that provides access to the blocking valve and it may also contain the lumen that provides access to the fixation balloon. The fixation balloon is inserted in a deflated state and inflated to hold the system in place. The fixation balloon remains inflated with the blocking valve providing continence and allowing voiding. The blocking value may be a conventional valve that is activated remotely or it may be controlled via a lumen or string that connects to the valve and provides access from outside the body. The blocking valve may be a string that expands when relaxed and narrows when stretched.

16 Claims, 14 Drawing Sheets

FIG. 11B

FLOW-AROUND VALVE WITH CONTOURED FIXATION BALLOON AND CHANNEL BLOCKING MEANS

This application is a CIP of application Ser. No. 08/896,072 filed Jul. 17, 1997.

FIELD OF THE INVENTION

This invention relates generally to devices that control incontinence and, more particularly, to urethral valves.

BACKGROUND OF THE INVENTION

Incontinence is a serious problem for many people and, in particular, for many females. Adult diapers may be used to capture leaking urine, or alternatively, urethral plugs or valves may be used to provide continence. Urethral plugs and values are positioned in the urethra to block urine flow. The plug is removed from the urethra for urination. The valve remains in place and opens to allow urine to flow through the valve, and out of the body.

The urethral plug is used once and then thrown away. After voiding, a new plug must be inserted to again provide continence. Over time, with the repeated insertion and removal of the plugs, the lining of the urethra may become irritated.

Each time a plug is inserted, it carries bacteria from the meatus and the distal end of the urethra into the proximal end of the urethra. The bacteria may infect the urethra, particularly if the lining is irritated. Further, the bacteria may migrate up into and infect the bladder.

The urethral valve remains in the urethra over some period of days. The typical valve extends through the urethra to the outside of the body, where a mechanism for opening the valve is accessible to the user. The valve thus provides a path for bacteria to travel from the meatus and the distal end of the urethra to the proximal end of the urethra and the bladder. Further, the insertion of the valve into the urethra often irritates the lining of the urethra, and thus, promotes bacterial growth.

SUMMARY OF THE INVENTION

An improved urethral valve system includes a valve balloon that inflates to provide continence and in certain embodiments deflates to allow urine to flow around the balloon. A small-diameter catheter is attached to the balloon and extends through the urethra to provide access to the balloon from outside the body. When the urine flows around the balloon, the urine also flows around the catheter and through the urethra, and out of the body through the meatus. The urine cleanses the valve balloon, catheter and the urethra of bacteria, and thus, minimizes infection. In an alternative embodiment the valve balloon remains inflated during urination, and is moved from a position in which it blocks urine flow through the neck of the bladder to a position in which urine flows around the balloon, out of the neck of the bladder, around the catheter and through the urethra.

The valve system may be anchored in the bladder, to prevent the system from being drawn from the body by the flow of urine. The anchor may be, for example, a balloon, which may be either the same balloon that provides continence or a second balloon. If a single balloon is used both to anchor the system and provide continence, the balloon may deflate to a shape that retains the balloon in the bladder against the flow of urine. Alternatively, the system may include a mechanical means to hold the deflated balloon in the bladder, such as, for example, rubber fingers that extend from the base of the balloon beyond the neck of the bladder.

The valve balloon may instead be positioned within the urethra, with an anchoring mechanism positioned in the bladder to hold the deflated valve balloon in place during urination.

The catheter runs from the valve balloon through the urethra to the outside of the body, and includes a check valve at the end that is accessible to the user. To inflate the balloon, the user attaches to the check valve a small pump that supplies air or a liquid such as water to inflate the balloon. To deflate the balloon, the user manipulates the check valve to allow the water or air to drain from the balloon. The catheter has a small diameter, since urine flows around the catheter and not through it.

The valve system preferably includes an everting mechanism that provides non-irritating delivery of the valve and/or anchoring balloons to the body. An everted membrane unrolls to provide a path through the urethra for the balloons, to prevent irritation of the lining of the urethra. The everting mechanism also prevents bacteria from being drawn from the meatus and distal end of the urethra into the proximal end of the urethra and into the bladder.

BRIEF DESCRIPTION OF THE DRAWINGS

The invention description below refers to the accompanying drawings, of which.

DETAILED DESCRIPTION OF ILLUSTRATIVE EMBODIMENTS

Figure 1A:
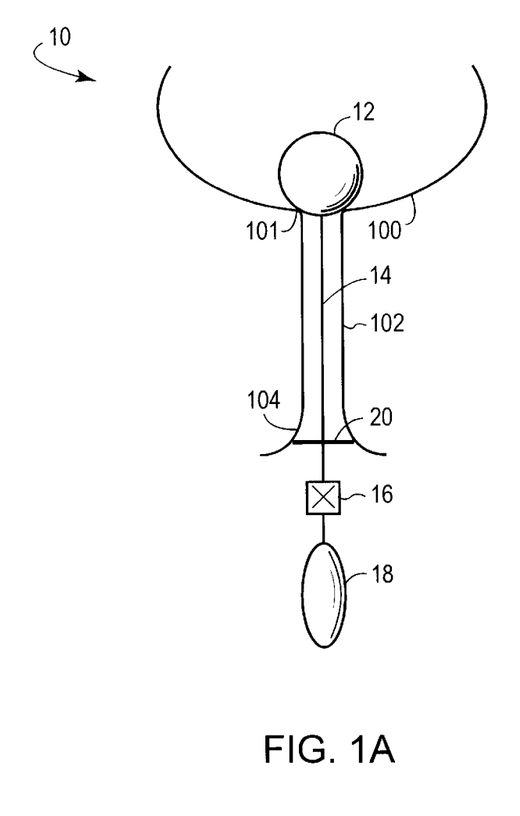
FIG. 1A is an illustration of a first embodiment of a urethral valve system constructed in accordance with the invention providing continence.
Figure 1B:
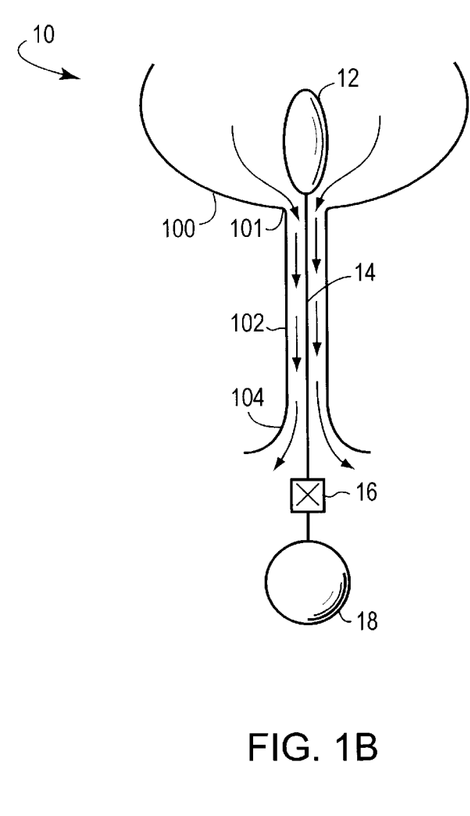
FIG. 1B is an illustration of the first embodiment of the urethral valve system allowing urination.

Referring to FIGS. 1A and 1B, a urethral valve system 10 includes a valve balloon 12 that is positioned in a bladder 100 to obstruct the flow of urine from the bladder. The diameter of the balloon 12 must be large enough essentially to seal the neck 101 of the bladder 100 and prevent urine flow from the bladder. A small-diameter catheter 14 attaches to the balloon 12 and extends through the urethra 102 and past the meatus 104. A check valve 16, which is closed to retain within the system the substance, such as air or water, that is used to inflate the balloon 12, extends slightly below the meatus 104. A pump 18, which is removably attached to the check valve 16, provides, for example, the water to the system. When the balloon is inflated, as depicted in FIG. 1A, the balloon provides continence.

For urination, a user deflates the balloon 12 through the check valve 16. As depicted by the arrows in FIG. 1B, when the balloon 12 is deflated urine flows around the balloon, through the neck 101 of the bladder 100, through the urethra 102 and around catheter 14, and out of the meatus 104. The urine flow cleanses the balloon 12 and the catheter 14 of bacteria in the same way that the body naturally cleanses the urethra, and thus minimizes the chances for infection from upwardly migrating bacteria.

The balloon 12 and the catheter 14 may also be coated with an antibacterial coating, to prevent colonization.

As depicted FIG. 1B, the pump 18 captures the water and retains it for use in re-inflating the balloon 12. The user may instead release the water from the system 10, and use fresh water to re-inflate the balloon.

The balloon is deflated for insertion into and removal from the bladder. Once deflated, the balloon is removed by gently pulling on the catheter 14.

For additional protection against the upward migration of both the system 10 and bacteria, a meatal collar 20 may be positioned slightly above the check valve 16. Further, the meatal collar 20, like the other system components, may be coated with an anti-bacterial coating to prevent colonization.

The balloon 12 and the catheter 14 may be made of any inflatable, non-reactive material, such as silicon. The catheter 14 has a small diameter since urine flows around the catheter rather than through the catheter.

Figure 2A:
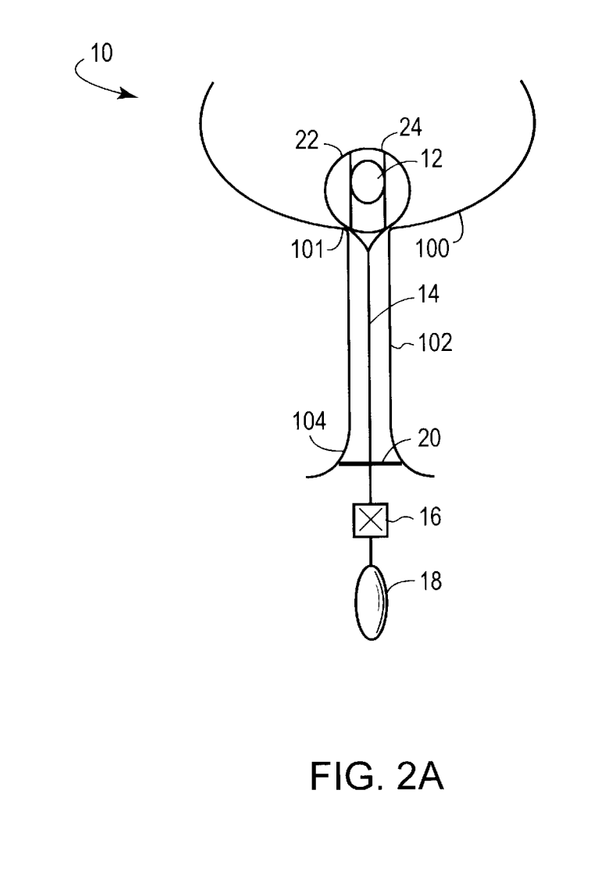
FIG. 2A is an illustration of a second embodiment of a urethral valve system constructed in accordance with the invention.
Figure 2B:
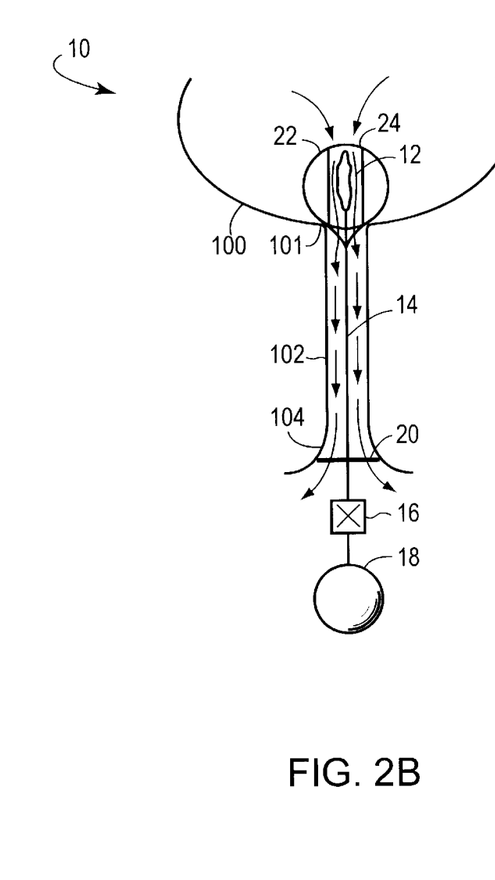
FIG. 2B is an illustration of the second embodiment of the urethral valve system allowing urination.

FIGS. 2A and 2B depict a second embodiment of the urethral valve system. In this embodiment, the valve balloon 12 is attached to a second, fixation balloon 22, which is included in the system to anchor it within the bladder 100. The fixation balloon in its inflated state, has a diameter that is larger than the neck 101 of the bladder 100, to ensure that the system will not be pulled from the bladder by the flow of urine. The fixation balloon 22 includes a channel 24 that houses the valve balloon 12. The valve balloon may be attached to the fixation balloon by, for example, webbing (not shown) through which urine can readily flow.

When the valve balloon 12 is inflated, the channel 24 is sealed to provide continence. When the valve balloon is deflated, as depicted in FIG. 2B, the channel 24 is opened and urine flows through the channel and around the valve balloon 12. The fixation balloon remains inflated during urination and holds the system in position against the flow of urine. As discussed above, the urine flow cleanses bacteria from the balloon 12 and the catheter 14, which comes in contact with the meatus 104 and the distal end of the urethra. The cleansing minimizes the upward migration of bacteria.

FIGS. 3A–3D depict a third embodiment of the urethral valve system. In this embodiment, the valve balloon 12 acts also as the anchoring mechanism. There is thus no need for the fixation balloon 22 (FIG. 2A). In this embodiment, the valve balloon 12 deflates into a shape 12b or 12c that includes one or more elongated arms 30. Urine can then flow around the arms 30, through the neck 101 of the bladder 100, around the catheter 14 and through the urethra 102, and out of the meatus 104.

Figure 3A:
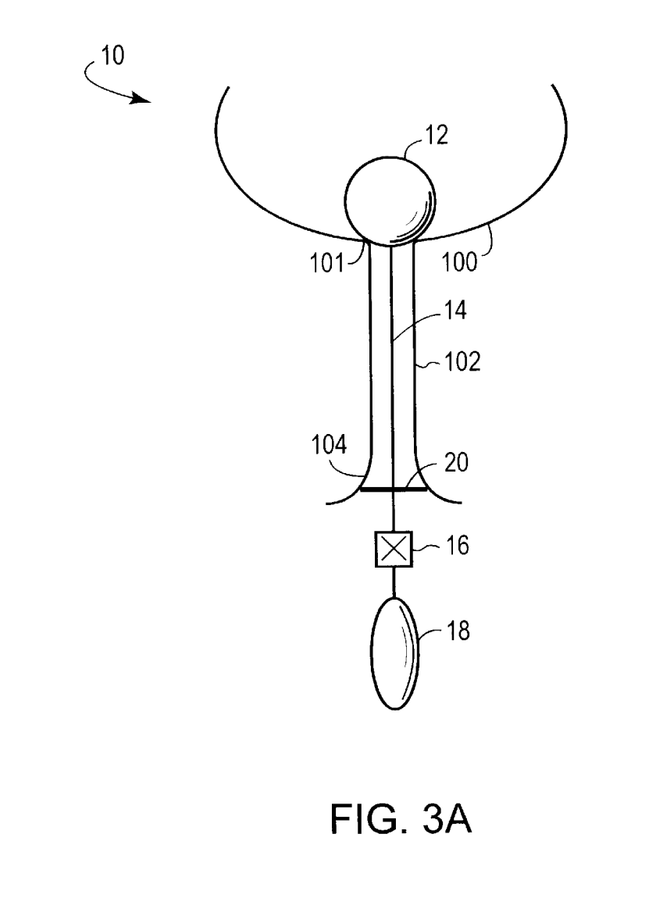
FIG. 3A is an illustration of a third embodiment of a urethral valve system constructed in accordance with the invention.
Figure 3B:
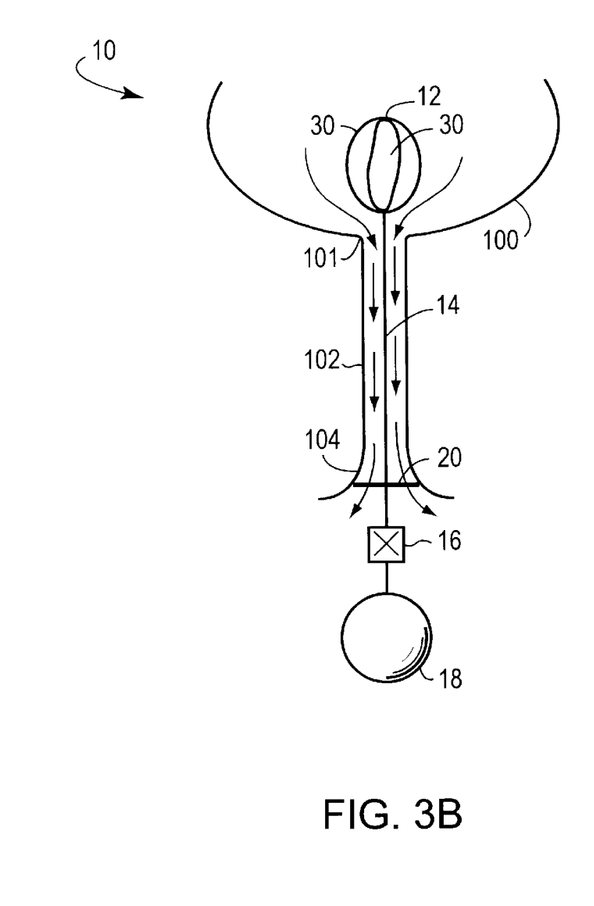
FIG. 3B is an illustration of the third embodiment of the urethral valve system allowing urination.
Figure 3C:
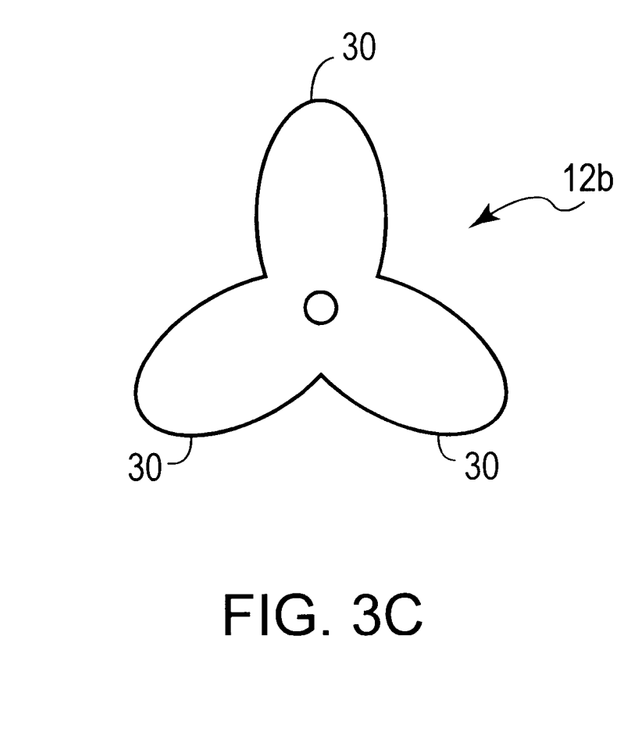
FIGS. 3C–D are top views of a component of the system of FIG. 3B.
Figure 3D:
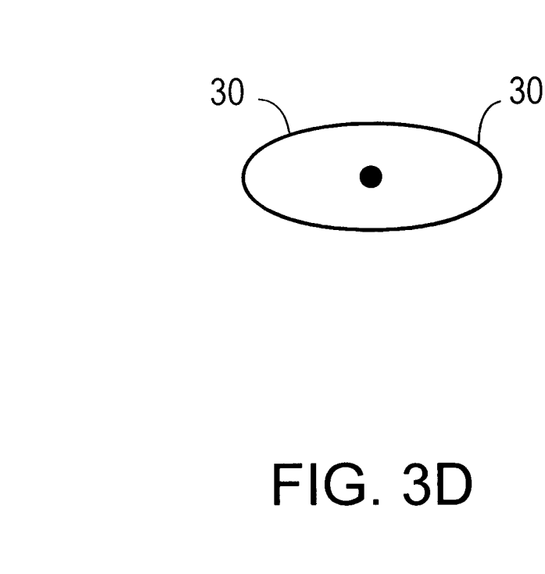

The arms 30 have a span that is longer than the width of the neck 101 of the bladder 100, and they thus, retain the balloon 12 in the bladder against urine flow. The arms 30 are also flexible so that the balloon can be removed from the bladder by gently pulling on the catheter 14.

Figure 4A:
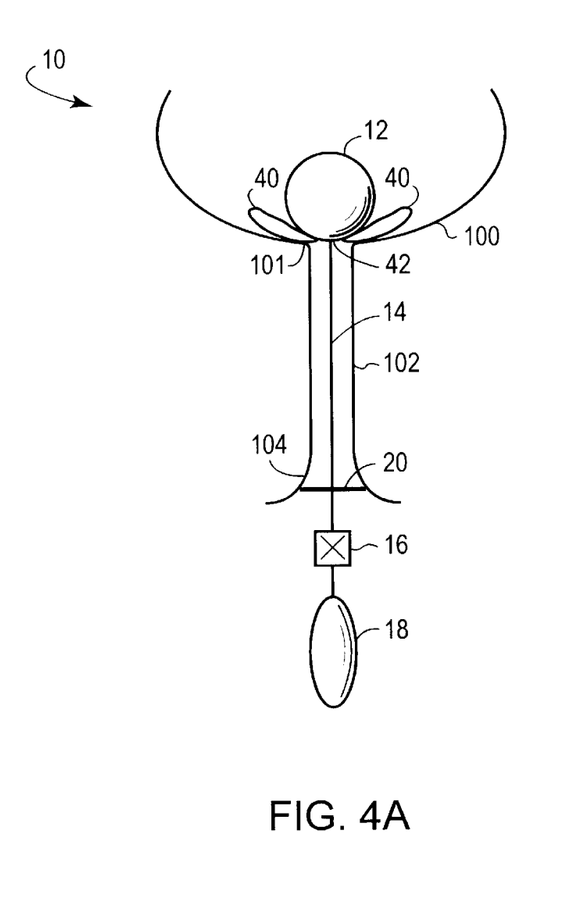
FIG. 4A is an illustration of a fourth embodiment of a urethral valve system constructed in accordance with the invention.
Figure 4B:
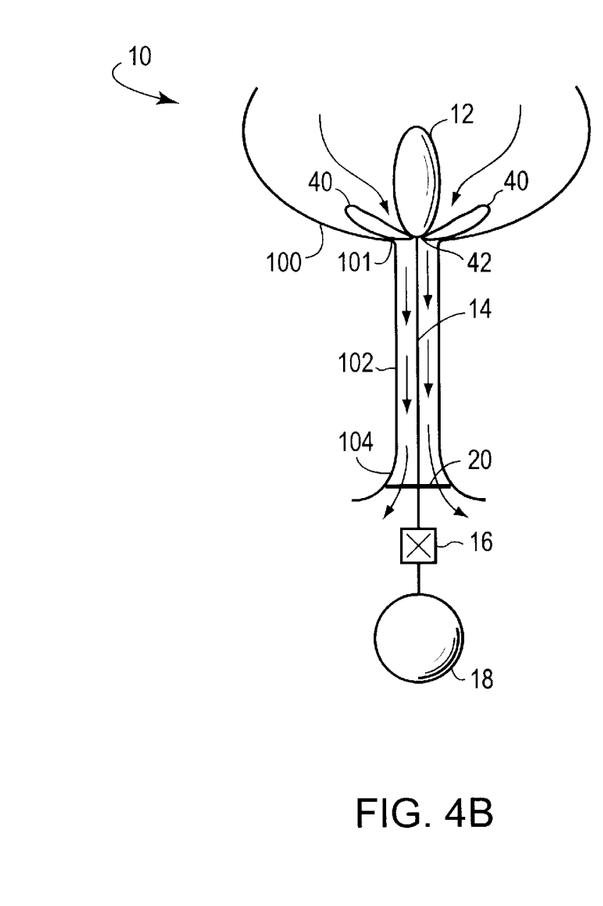
FIG. 4B is an illustration of the fourth embodiment of the urethral valve system allowing urination.

Referring now to FIG. 4, a fourth embodiment of the urethral valve system includes flexible fixation tabs 40 that extend outwardly from a base 42 of the balloon 12. When the balloon 12 is deflated, the tabs 40 hold the balloon in place at the neck 101 of the bladder 100. Urine then flows around the balloon and the tabs, out of the bladder, around the catheter 14 and through the urethra, and out of the body through the meatus.

Figure 5A:
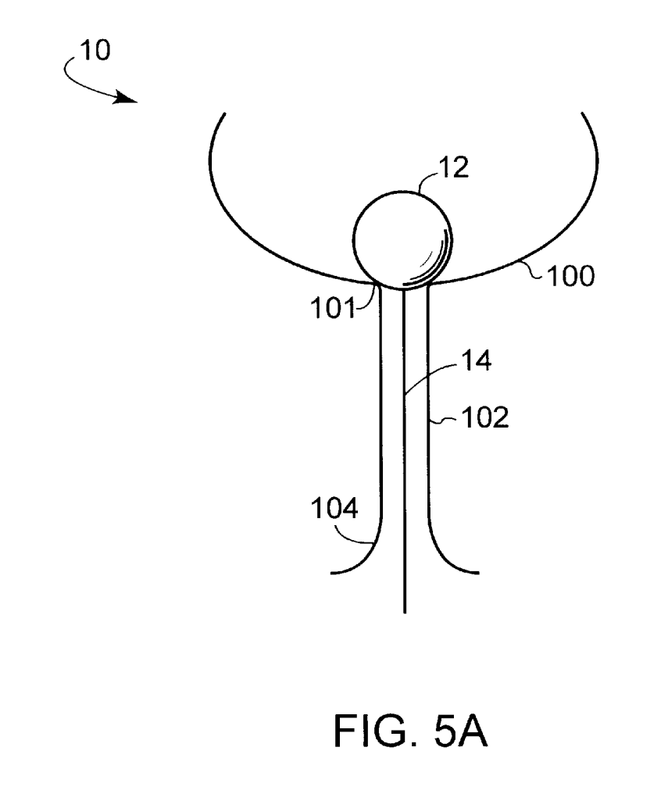
FIG. 5A is an illustration of a fifth embodiment of a urethral valve system constructed in accordance with the invention.
Figure 5B:
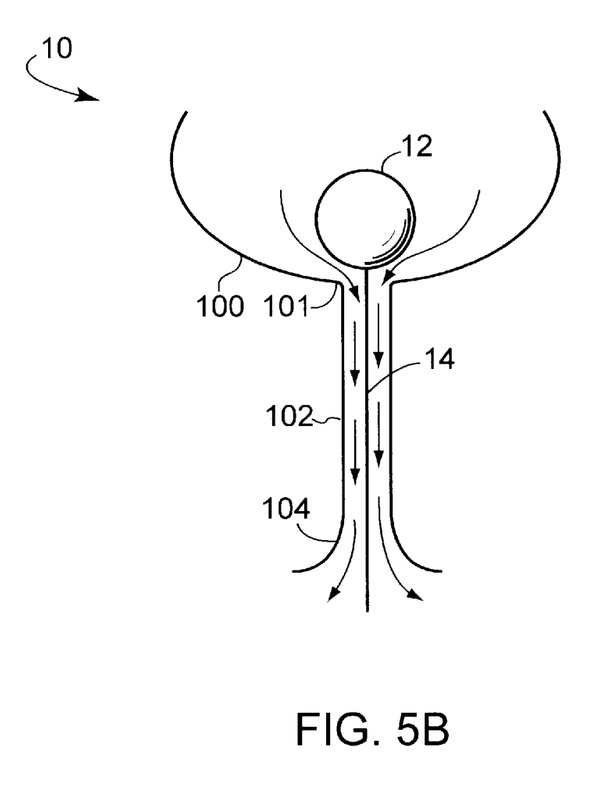
FIG. 5B is an illustration of the fifth embodiment of the urethral valve system allowing urination.

In FIG. 5, the catheter 14 is stiffened somewhat, so that a user can move the valve balloon 12 away from the neck 101 of the bladder. Urine can then flow out of the neck of the bladder 100 and through the urethra 102. To reposition the valve balloon 12 in the neck of the bladder the user then gently pulls on the catheter 14.

Figure 6A:
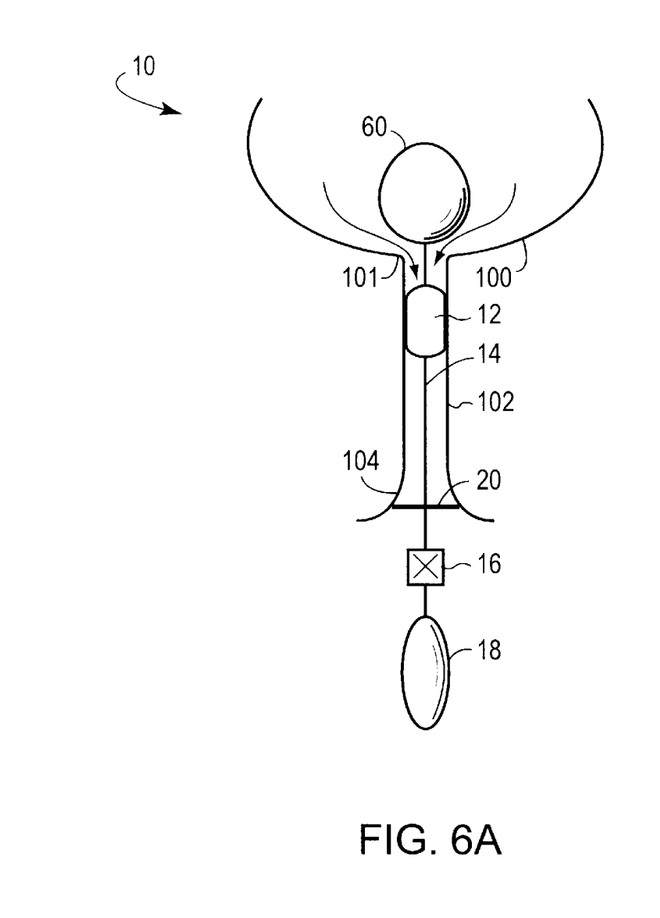
FIG. 6A is an illustration of a sixth embodiment of a urethral valve system constructed in accordance with the invention.
Figure 6B:
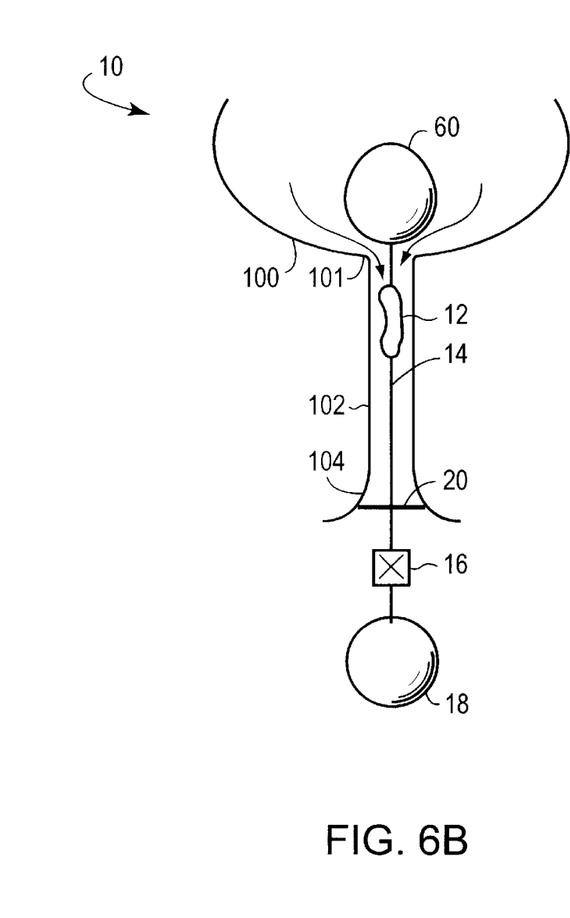
FIG. 6B is an illustration of the sixth embodiment of the urethral valve system allowing urination.
Figure 7:
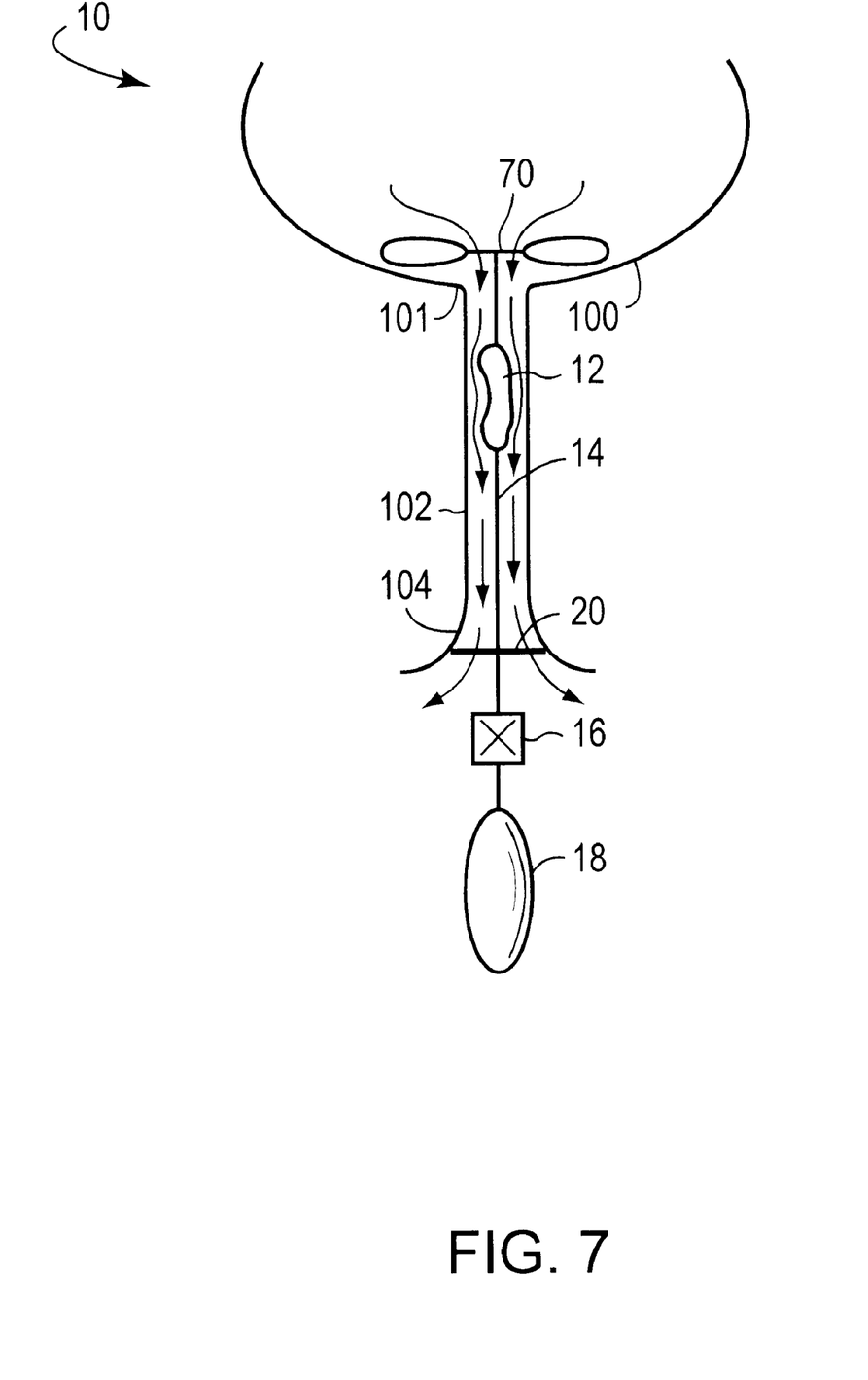
FIG. 7 is an illustration of a seventh embodiment of the urethral valve system allowing urination.

As shown in FIGS. 6 and 7, the valve balloon 12 may be positioned in the urethra 102. When the valve balloon 12 is inflated, it provides continence by blocking the flow of urine in the urethra. When the balloon 12 is deflated, urine flows around the balloon and the attached catheter 14 and through the distal end of the urethra 102 and out of the body through the meatus 104.

Different types of fixation devices may be used to retain the system in place against the flow of urine. For example, a second balloon 60 may be positioned in the bladder, as shown in FIG. 6. Alternatively, as depicted in FIG. 7, foldable arms 70, which are inserted and then unfolded in the bladder 100, may be used to anchor the system.

Figure 8:
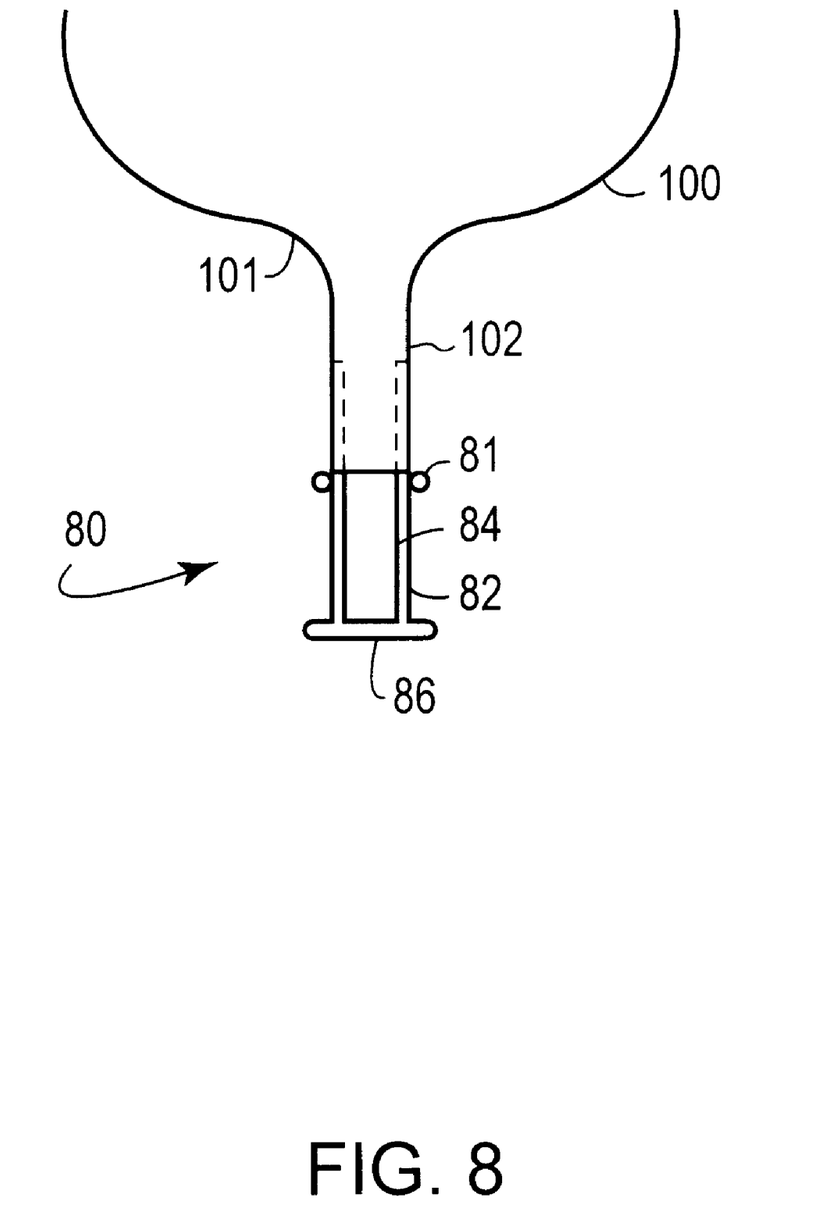
FIG. 8 is an illustration of an everting mechanism that may be used with the urethral valve systems discussed herein.

FIG. 8 depicts an everting mechanism 80 that may be used for introduction of the valve system 10 (FIGS. 1–7) into the body through the urethra. The everting mechanism 80 includes an introducing device 82, such as, for example, a tube, that a user inserts into the distal end of the urethra 102 up to a stop 81. The tube contains an everted membrane 84 with one end held by the stop. The membrane 84 unrolls, as depicted by dotted lines, as an advancing device 86 is pushed deeper into the urethra. The unrolled membrane then provides a path through which the valve system may be inserted, without coming into contact with the lining of the urethra. After the system is fully inserted, the membrane 84 is removed from the body.

There is essentially no relative motion between the membrane 84 and the walls of the urethra as the membrane unrolls. Accordingly, the lining of the urethra is not irritated by the insertion of the membrane, or the introduction of the valve system through the membrane.

Further, the surface of the membrane that comes in contact with the lining of the urethra does not come in contact with the distal end of the urethra. Accordingly, bacteria from the distal end of the urethra is not carried deeper into the urethra or into the bladder by either the membrane, or the valve system that is introduced through the membrane.

Figure 9:
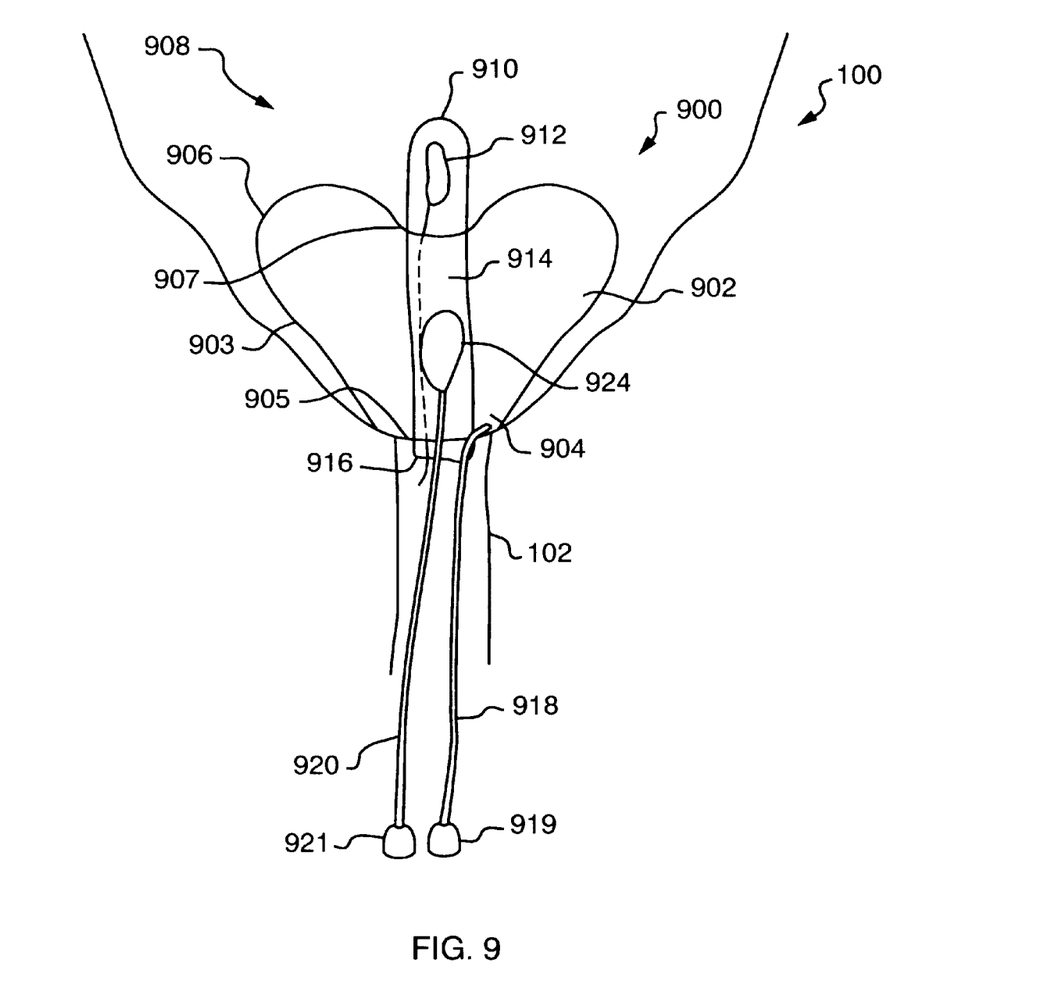
FIG. 9 is an alternative embodiment of the system of FIG. 2.

Referring now to FIG. 9, another embodiment 900 of the urethral valve system is depicted. In this embodiment, the fixation balloon 902 is contoured to the geometry of the bladder 100 near the opening to the urethra 102. The fixation balloon 902 is narrower on an end 904 that is closest to the urethra when the balloon is in place in the bladder, and wider on an opposite end 906. The fixation balloon thus provides a good seal at the bladder opening, and prevents urine from leaking around the balloon.

The contoured fixation balloon 902 is depicted in the drawing attached to an end 910 of a pliable Foley-type catheter 908. The catheter 908 has an opening 912 at the top end and a channel 914 through which urine flows out of the bladder. The arrows in the drawing indicate urine flow. An opposite end 916 of the channel 914 opens at the top end of the urethra. Urine thus flows out of the channel 914, into the urethra and around lumens 918 and 920 that extend through the urethra. The lumens, respectively, provide access to the fixation balloon 902 and to a valve balloon 924, which is positioned within the channel 914. The valve balloon 924 inflates to block urine flow through the channel 914, deflates to allow urine to flow through the channel and around the lumens, and then again inflates to block urine flow and provide continence. The fixation balloon 902 deflates for insertion and removal of the system, but otherwise remains inflated in the body. The balloons 902 and 924 are inflated and deflated through check valves 921 and 919.

The contoured fixation balloon 902, which is fixed to the catheter 908 at inside edges 905 and 907 of top and bottom ends 904 and 906, also acts as a shock absorber for the system 900. The fixation balloon moves at its outer edge 903 relative to the catheter 908 in response to, for example, a contraction in the bladder. The contoured fixation balloon can thus be comfortably worn by a user over an extended period of time, such as, for example, a day or a week.

Figure 10A:
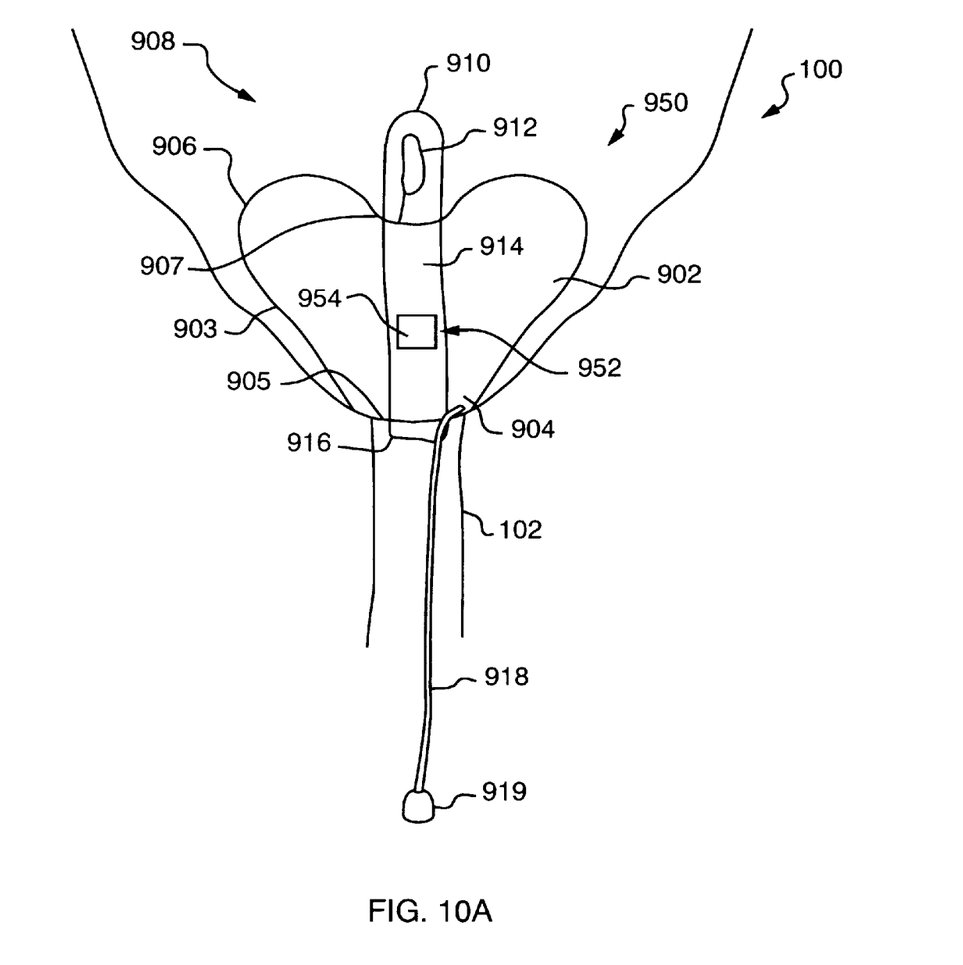
FIGS. 10A–B are an alternative of the system of FIG. 9.
Figure 10B:
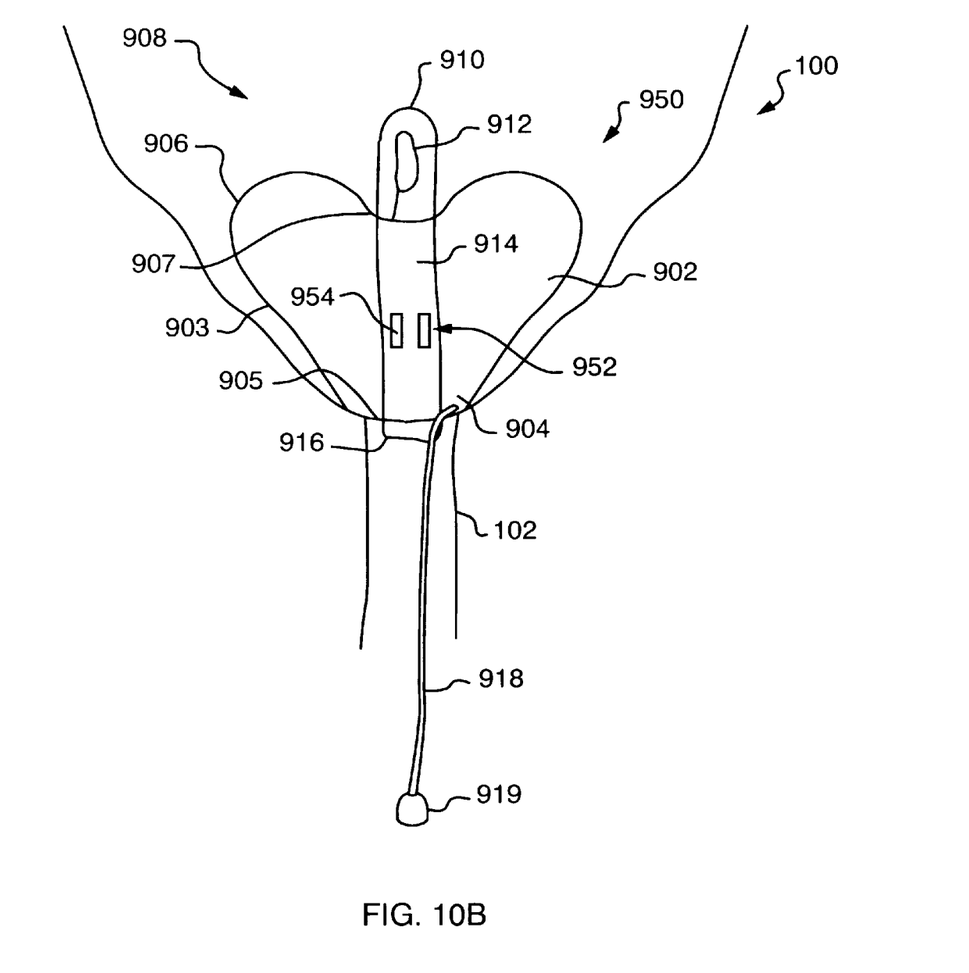

Referring now to FIGS. 10A–10B, an alternative system 950 to the system 900 of FIG. 9 is depicted. The system 950 preferably includes the contoured fixation balloon 902 and, in the channel 914 through the catheter 908, a blocking means 952 that has two states, namely, a first state in which it blocks urine flow through the channel and a second state in which it allows the urine to flow through the channel. In the second state, the blocking means 952 allows urine to flow around or through the blocking means 952, and then through an open end 916 of the channel 914, though the urethra and around the lumin 918.

The blocking means 952 may be, as depicted in the drawing, a valve 954 that opens and closes in response to signals from outside the body. The valve may be magnetically activated by signals from a remote device, or it may be activated by other types of signals such as, for example, low-power microwave signals.

The urine flow through the urethra and around the lumen 918 inhibits bacterial migration from the urethra into the bladder, as discussed above, regardless of whether urine flows around the valve 954 or through the valve 954.

Figure 11A:
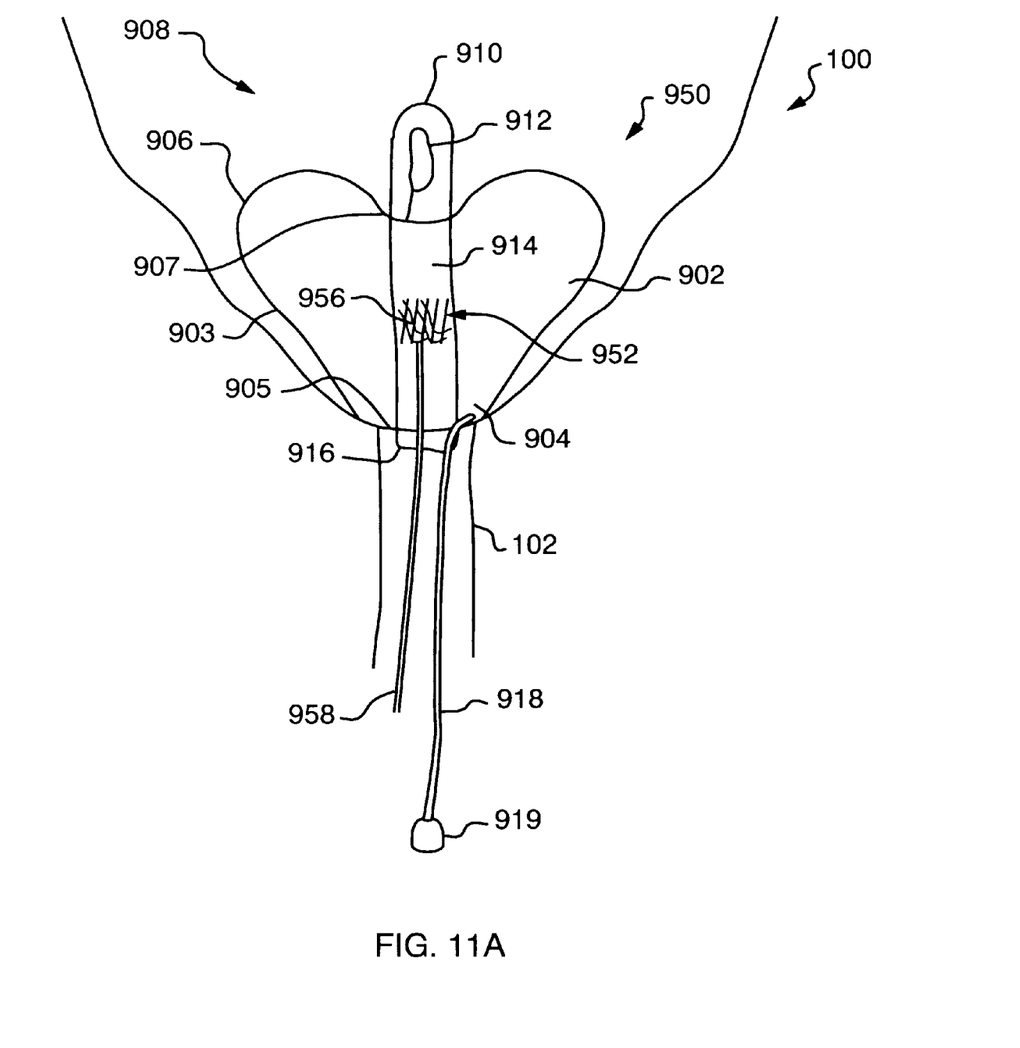
FIGS. 11A–B are an alternative embodiment of the system of FIG. 10.
Figure 11B:
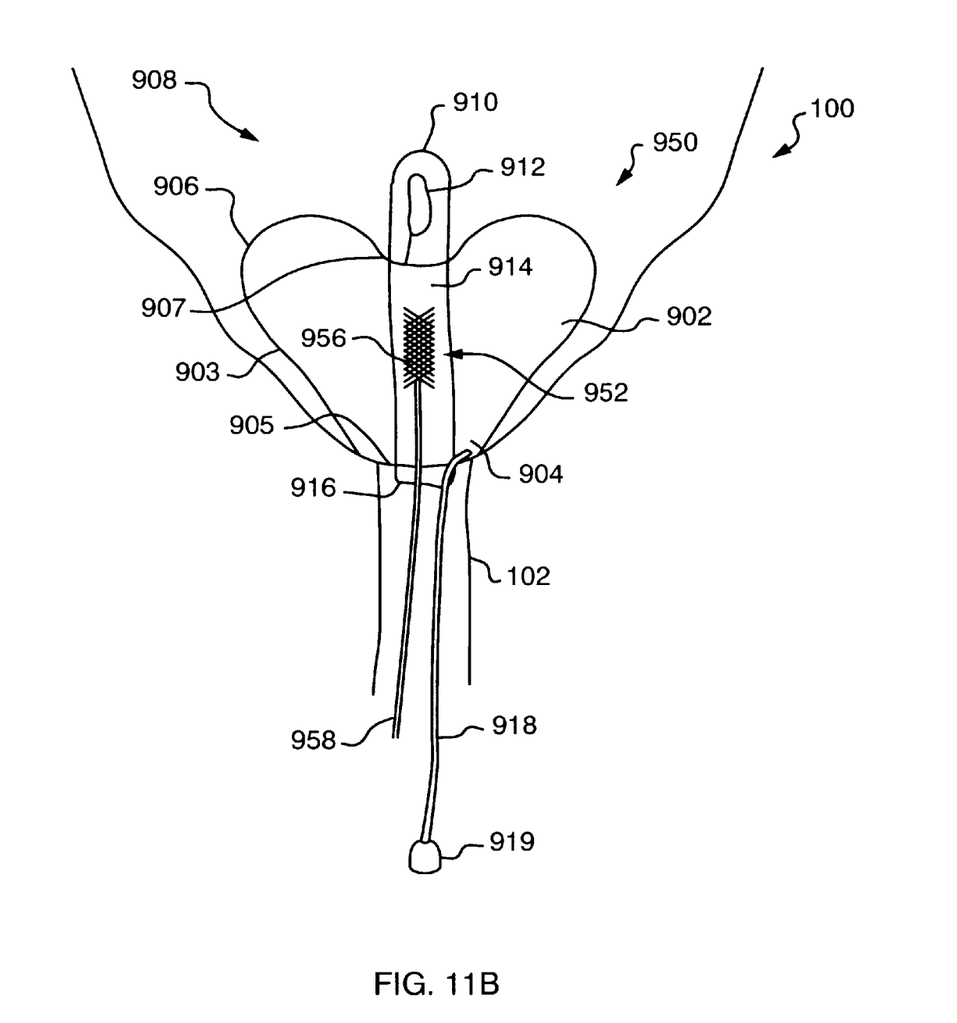

Alternatively, as depicted in FIGS. 11A–B, the blocking means 952 may be a braided string 956 that in a relaxed state fills all or a portion of the channel 914. A user gently pulls one end 958 of the string, to stretch and thus narrow and lengthen the braid, and open the channel for voiding. The user continues to hold the end 958 of the string while voiding, and then releases the end of the string. The string then relaxes to again block the channel and provide continence. The positioning of the string inside the channel prevents the movement of the string from irritating for example, the walls of the urethra.

The string 956 may be made of, for example, spring steel, and may be coated with an anti-bacterial coating. As discussed, the string is cleansed when urine flows around it during voiding, and thus, bacterial migration over the string is inhibited.

The blocking means 952 may be any type of two-state valve that blocks and unblocks the channel 914. The blocking means 952 may be used also in combination with, for example, the fixation balloon 22 depicted in FIG. 2, and obtain some or all of the advantages discussed herein. Alternatively, the blocking means 952 may be used with alternative anchoring mechanisms, that hold the catether 910 in place at the opening of the bladder to the urethra.

As discussed with reference to FIG. 8, each system may include an everting mechanism, for ease of insertion. Also, a meatal collar 20 (FIG. 1) may be included, as needed, to prevent upward migration of the system into the bladder.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. An incontinence system for controlling urine flow from a bladder through a urethra, the system including:

A. anchoring means for holding the system in position in the body;

B. a channel from the bladder to a proximal end of the urethra;

C. blocking means positioned in the channel to block urine flow through the channel when the blocking means is in a first state and to allow urine to flow around the blocking means, through the channel to the proximal end of the urethra, and through the urethra when the blocking means is in a second state;

D. activation means for controlling the state of the blocking means.

2. The system of claim 1 wherein the channel is a catheter.

3. The system of claim 1 wherein the anchoring means is a fixation balloon, and the system further includes a lumen for providing access to the fixation balloon from outside the body for:
  i. inflating the fixation balloon after insertion, to hold the fixation balloon in the bladder, and
  ii. deflating the fixation balloon when the fixation balloon is to be removed from the body, with urine flowing around the lumen when the blocking means is in the second state.

4. The system of claim 3 wherein the fixation balloon having a shape that is contoured to the bladder and the catheter extends through the balloon.

5. The system of claim 1 further including an everting mechanism.

6. The system of claim 1 wherein the blocking means is a valve, and the activation means activates the valve from outside the body.

7. The system of claim 1 wherein the blocking means is string that in the first state expands to fill a portion of the channel and in a second state narrows to allow urine to flow around the string and through the channel and the urethra, and the activation means is an end of the string that is moved from a first position associated with the first state to a second position associated with the second state.

8. The system of claim 7 wherein the string is braided.

9. The system of claim 7 wherein the string is made of steel.

10. The system of claim 7 wherein the portion of the channel is the entire channel.

11. An incontinence device including:

A. a fixation balloon that has a deflated state and an inflated state, the fixation balloon being positioned in the body in a deflated state and inflated to prevent urine flow around the balloon from a bladder, the fixation balloon being contoured to the shape of the bladder, and including a channel through which urine is directed from the bladder;

B. blocking means that is positioned in the channel of the fixation balloon, the blocking means having a first state that prevents urine flow through the channel and a second state that allows urine to flow through the channel;

C. activation means for controlling the state of the blocking means; and

D. a lumen for providing access to the fixation balloon from outside the body, the lumen being sized and positioned such that urine flows around the lumen when the blocking means is in a second state.

12. The incontinence device of claim 11 wherein the blocking means is a valve that opens to allow urine to flow through the channel and closes to prevent urine flow through the channel.

13. The incontinence device of claim 12 wherein the activation means controls the state of the valve from outside the body.

14. The incontinence device of claim 12 wherein the valve opens to allow urine to flow through the valve.

15. The incontinence device of claim 12 wherein the valve opens to allow urine to flow around the valve.

16. The incontinence device of claim 11 wherein the blocking means is string that in the first state expands to fill a portion of the channel and in a second state narrows to allow urine flow through the channel around the string, and the activation means is an end of the string that is moved from a first position associated with the first state to a second position associated with the second state.

* * * * *